(12) United States Patent
Wagner et al.

(10) Patent No.: US 6,890,134 B1
(45) Date of Patent: May 10, 2005

(54) METHOD OF PRODUCING ENDODONTIC INSTRUMENTS

(75) Inventors: Ingo Wagner, Woerthsee (DE);
Michael Knee, Peissenberg (DE);
Andreas Nitsch, Puergen (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 09/958,308

(22) PCT Filed: Mar. 8, 2000

(86) PCT No.: PCT/EP00/01992

§ 371 (c)(1),
(2), (4) Date: Mar. 8, 2002

(87) PCT Pub. No.: WO00/61026

PCT Pub. Date: Oct. 19, 2000

(30) Foreign Application Priority Data

Apr. 9, 1999 (DE) ................. 199 16 103

(51) Int. Cl.⁷ .............................. B23C 3/32
(52) U.S. Cl. ................. 409/131; 409/66; 409/65; 409/76; 409/165; 76/115; 433/102; 433/224
(58) Field of Search ............. 409/131, 65, 66, 409/72, 75, 76, 77, 78, 157, 161, 165; 433/81, 433/165, 224, 102; 76/108.1, 108.6, 115

(56) References Cited

U.S. PATENT DOCUMENTS

| | | | | |
|---|---|---|---|---|
| 141,760 A | * | 8/1873 | Card ................... | 409/76 |
| 164,115 A | * | 6/1875 | Weaver et al. ......... | 409/76 |
| 324,845 A | * | 8/1885 | Johnson ............... | 409/70 |
| 367,894 A | * | 8/1887 | Cox, Jr. ............... | 409/73 |
| 566,966 A | * | 9/1896 | Clausen ................ | 409/69 |
| 1,082,589 A | * | 12/1913 | Hardy ................. | 409/189 |
| 1,097,839 A | * | 5/1914 | Best ................... | 409/76 |
| 2,197,825 A | * | 4/1940 | Hollis ................. | 409/67 |
| 3,463,050 A | * | 8/1969 | Machen ................ | 409/70 |
| 4,934,934 A | * | 6/1990 | Arpaio et al. .......... | 433/102 |
| 5,184,926 A | * | 2/1993 | Hemmings ............ | 408/226 |
| 5,820,309 A | * | 10/1998 | Mihic ................. | 407/50 |
| 5,882,198 A | * | 3/1999 | Taylor et al. .......... | 433/102 |
| 5,902,106 A | * | 5/1999 | McSpadden ........... | 433/102 |
| 6,299,445 B1 | * | 10/2001 | Garman ............... | 433/102 |
| 2004/0229188 A1 | * | 11/2004 | Lewis et al. .......... | 433/102 |

FOREIGN PATENT DOCUMENTS

| | | | |
|---|---|---|---|
| DE | 1284255 | | 11/1968 |
| DE | 34 36 636 C2 | | 4/1985 |
| FR | 521180 | * | 7/1921 |
| JP | 80873 | * | 7/1978 |
| SU | 1563857 | * | 5/1990 |

OTHER PUBLICATIONS

W. Beitz, et al., "Handbook for Mechanical Engineering" Dubbel, 1997.
Root channel treatment with rotary equipment—a systematic treatment concept for practice (Quintessenz 50, 9, 878-889).

* cited by examiner

*Primary Examiner*—Daniel W. Howell
(74) *Attorney, Agent, or Firm*—Crowell & Moring LLP

(57) ABSTRACT

Methods for manufacturing endodontic instruments are provided. Methods relate to milling a blank with a cutting process to shape the instrument. Instruments so produced are also provided.

19 Claims, 4 Drawing Sheets

METHOD OF PRODUCING ENDODONTIC INSTRUMENTS

The invention relates to a method for producing endodontic instruments from a blank in rod or wire form.

Endodontic instruments are used in particular in a dental root canal treatment. They are used to treat the diseased root canal. These instruments may, for example, be small reamers, drills and files of a very wide range of geometric shapes and designs.

Endodontic instruments are usually manufactured from blanks in rod or wire form with a diameter of approximately 0.3 to 3 mm. These instruments are relatively complex to produce, requiring complex abrasive processes. It is attempted, by using grinding wheels which are adapted in a complicated way to the process and have specially defined parameters, to achieve satisfactory results.

It is known from U.S. Pat. No. 5,655,950 to manufacture endodontic instruments from a metal alloy comprising nickel and titanium fractions by grinding. Parameters such as the relatively low feed rate of, for example, up to 250 mm/min, with the need to precisely maintain the circumferential speed of the grinding wheel, lead to a high manufacturing outlay for each instrument. A drawback of this method is that microcracks are easily formed on account of the superelasticity of the nickel-titanium alloys. The formation of microcracks is also promoted by the fact that the abrasive grains do not have a regular geometry and a high grinding speed is used.

The machining of metal blanks with dimensions of larger than a few millimeters by metal-removing shaping with a geometrically defined cutting edge and cutting removal, for example by milling, drilling, cutting or turning, is known in other engineering fields. However, in this case, the success of metal-removing machining of metal blanks by milling is dependent on the materials properties of the metal blank.

It is also known to machine metal blanks by high-speed-cutting milling (HSC milling). This milling method is distinguished by a high cutting speed, which allows heat to be dissipated via the chips which are removed.

The invention is based on the object of producing high-quality endodontic instruments in an economic way.

According to the invention, this object is achieved by the provision of a method as described in the claims.

The endodontic instruments are in this case produced by milling methods using milling cutters with a geometrically defined cutting edge and cutting removal, in particular by high-speed-cutting milling.

The method according to the invention has the following advantages:

While in the known manufacture of endodontic instruments by grinding the known grinding wheels become clogged by shaving removal of material, in the method according to the invention the cutting removal of material means that the cutting edges of the milling cutters do not become blocked with chips. This allows the precise and defined production and machining of a large number of endodontic instruments without the milling cutters having to be cleaned and/or replaced.

For example, when using titanium-coated hard metal milling cutters, it is possible to achieve a particularly high service life while the cutting quality remains constant. This minimizes tool costs during the manufacturing process.

A further advantage is that the microcracks which are often observed during grinding in the machined material can be substantially avoided when using the present method.

The wire or blank is preferably guided in a special holder and can be held in an optimum position with respect to the cutting edges of the milling cutter by means of a support device. This holder preferably comprises a perforated disc for defined guidance of the wire. In this case, the milling cutter is preferably fitted slightly eccentrically, in order to prevent poor-quality removal of material at the low cutting-edge speed in the center of the milling cutter. The support device preferably has a block with a channel which is matched to the diameter of the blank or workpiece. The blank is preferably guided and supported in this channel during the machining, so that it cannot escape from the milling cutter. The block can be tracked in the radial direction by means of a spring, by means of a servomotor, hydraulically or pneumatically, in order to compensate for any reduction in diameter which could result from the milling. The tracking of the support device expediently takes place elastically and radially with respect to the blank in rod or wire form.

Even at high cutting speeds in the range from 10 to 300 m/min, preferably in the range from 50 to 200 m/min, with the associated rapid feed rates, the amount of heat introduced into the material is low, since the milling method means that the heat which is generated is dissipated via the chip. Consequently, the changes in the microstructure of the material, despite high and economical removal rates, are very low and therefore do not cause any deterioration in the original materials properties. The superelasticity of the endodontic instrument, which is desired by the user, is fully retained.

Furthermore, the surface quality in the micrometer range is of very high quality, since the formation of notches in the material is greatly reduced by the cutting machining. Consequently, it is possible to generate the exact cutting edges of defined sharpness without causing spalling, resulting in a positive quality in terms of sharpness and cutting capacity for the user.

Finally, the method according to the invention makes it possible to achieve unexpectedly high feed rates of the workpiece of up to 2000 mm/min, so that the production time for each instrument can be reduced considerably. Feed rates in the range from 20 mm/min to 1000 mm/min have proven advantageous.

In addition, it is possible to complete the entire removal of material down to the desired depth in order to form the shank or the flutes within a single feed operation, so that it is not necessary, as is often the case with grinding methods, to pass over the same part of the blank or wire two or three times. For these reasons, the number of instruments which it is possible to produce each year per machine is higher by a factor of up to five than with conventional grinding methods, even though the machine investment costs are similar.

When using CNC milling machines (CNC=computer numerical control), it is possible to achieve any conceivable form of endodontic instruments with a single type of machine by simply changing the program. Simply adjusting the manufacturing parameters (changing the program) eliminates the need for expensive, machine-specific refits.

HSC milling can be used in particular also for rapid and precise machining of superelastic nickel-titanium alloys with high cutting speeds, which was unexpected. However, the method is also suitable for machining materials which have a high tensile strength and may also have been hardened, such as steel and graphite.

Further advantages of this method are the ease of producing even complex geometries in a rod-shaped blank or wire by flexible positioning of the milling cutter. The method according to the invention can be used to mill all useful surface geometries, such as flutes, shanks and spirals.

Suitable milling tools are designed, for example, as two-tip end mills with standard cutting edges and are preferably coated with, for example, titanium nitrite (TIN), titanium carbonitride (TiCN), titanium aluminum nitride (TiAlN), CBN and polycrystalline diamond (PCD). A standard diameter for a suitable face-milling cutter lies in the range from 0.3 to 3 mm, preferably in the range from 0.5 to 2 mm. A setting angle for the milling tools in the range from 5 to 30°, preferably in the range from 10 to 20° C., has proven expedient.

The cross section of the blank in rod or wire form may be rounded (circular or elliptical) or polygonal (square, rectangular or triangular).

The invention is explained below using exemplary embodiments, without the intention being for the invention to be restricted by these embodiments. In the drawing.

Figure 1:
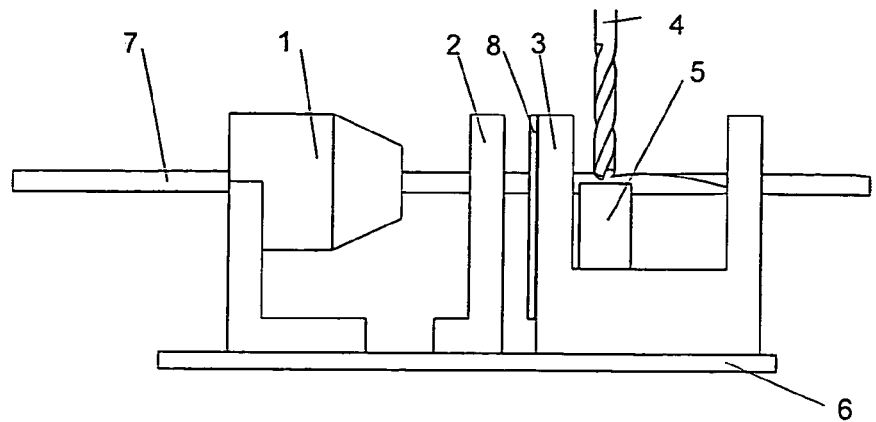
FIG. 1 shows a side view of an HSC milling machine, in which a blank is being machined by means of a centrally arranged milling cutter.

In the exemplary embodiments illustrated in FIGS. 1 to 9, a blank 7 which is in rod form and consists of a superelastic nickel-titanium alloy is being machined in a milling machine by means of an HSC milling cutter 4. The milling machine has a base plate 6, on which a guide receptacle 3 with an integral cutting device 8 and with a continuous support device 5 for guiding the blank 7, and a conventional feed unit comprising chuck 1 and outer support 2 are accommodated. The milling cutter 4 is held by a conventional milling cutter spindle, which is not shown. Its working area is precisely in the region of the support device 5.

During the machining, the blank 7, which is illustrated on the left, is pulled onward over an entire machining length between the chuck 1 and the outer support 2. The outer support 2 opens, and the rotatably mounted chuck 1 then pushes the blank 7 into the working area of the milling cutter 4 which provides the end of the rotating blank 7 with the desired geometry. Then, the desired surface geometry is imparted to the blank 7. In the process, the milling path is generated by a rotary movement of the chuck 1 in combination with a linear feed movement. To ensure a high level of precision, the machining takes place in a single pass. When the machining has been concluded, the workpiece can be cut off using the milling cutter 4 or a cutting device 8.

Different milling cutter geometries and positions relative to the workpiece or different setting angles of the milling cutter 4 enable different geometries to be formed in the blank 7. The variations allow the cutting geometry of the endodontic instrument which is to be manufactured to be optimized.

Figure 2:
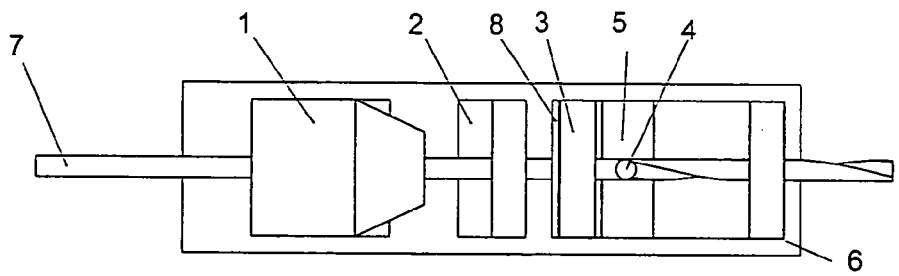
FIG. 2 shows a plan view of the HSC milling machine from FIG. 1.

In the exemplary embodiment shown in FIGS. 1 and 2, the milling cutter is set at right angles to and centrally on the blank 7. The cutting speed is very low in the center of the milling cutter 4, so that microcracks may form in the material of the blank 7 at this location. Such microcracks may be tolerable in some instruments.

The area of such microcracks can also be remachined in a second pass.

Figure 3:
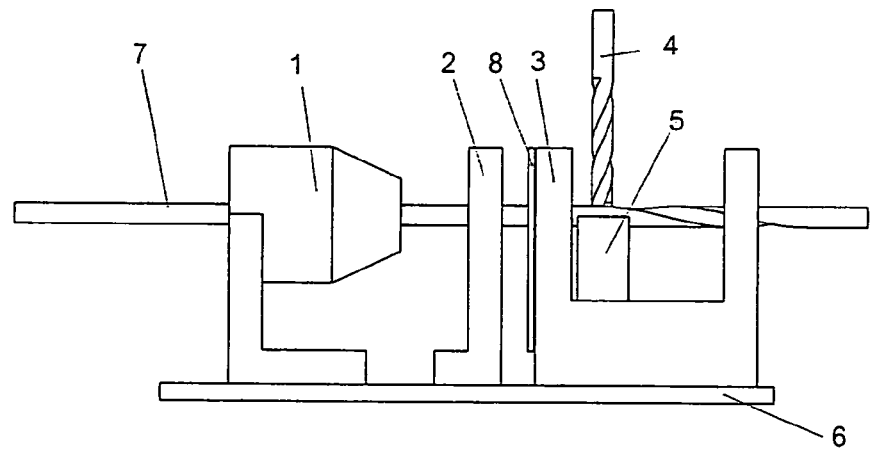
FIG. 3 shows a side view of an HSC milling machine, in which a blank is being machined by means of an eccentrically arranged milling cutter.
Figure 4:
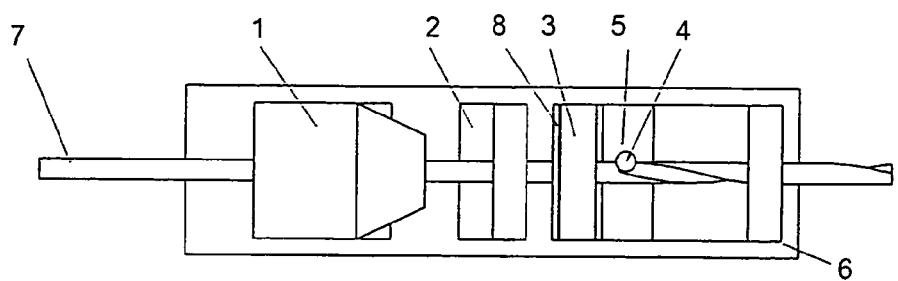
FIG. 4 shows a plan view of the HSC milling machine shown in FIG. 3.
Figure 5:
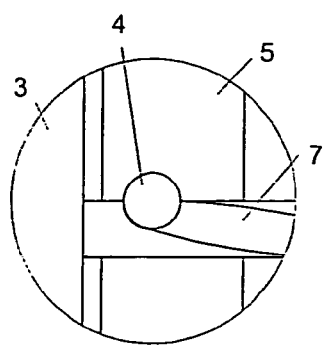
FIG. 5 shows a detailed view of FIG. 4 encompassing the milling region including milling cutter and support device.

In the exemplary embodiment shown in FIGS. 3 to 5, the milling cutter is set at right angles but eccentrically. The area of the milling cutter 4 which is close to the center therefore does not touch the blank, so that the cutting edges of the milling cutter 4 always have a high cutting speed at the points where they are in contact with the blank 7.

Figure 6:
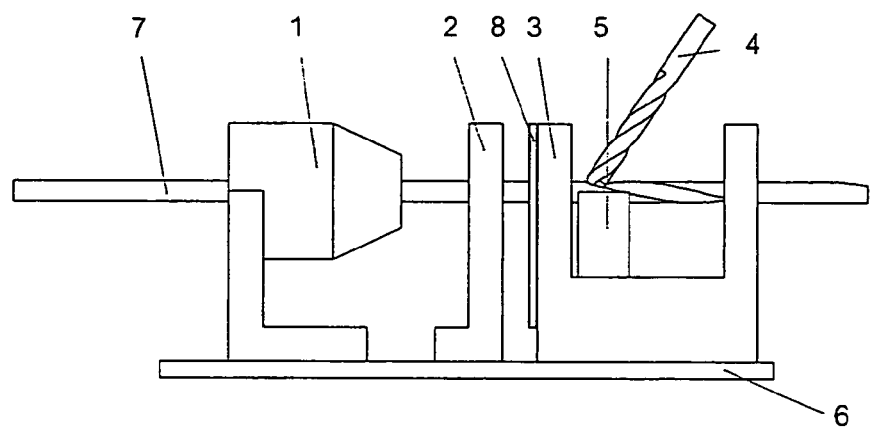
FIG. 6 shows a side view of an HSC milling machine, in which a blank is being machined by means of a milling cutter which is set at an angle.
Figure 7:
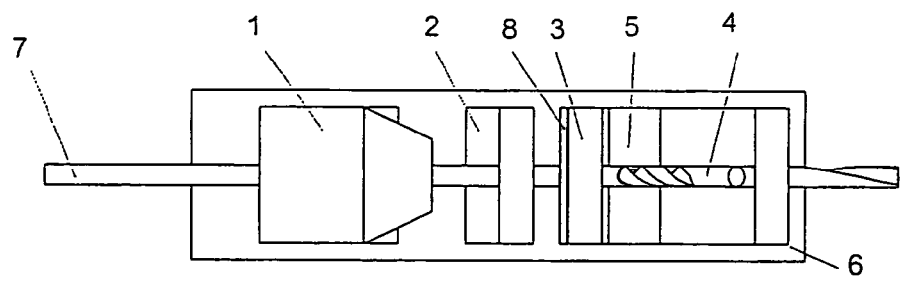
FIG. 7 shows a plan view of the HSC milling machine shown in FIG. 6.
Figure 8:
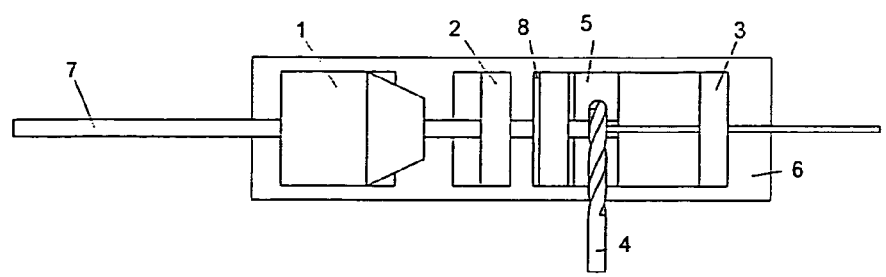
FIG. 8 shows a side view of an HSC milling machine, in which a blank is being machined by means of a milling cutter which is set as a cylindrical milling cutter.
Figure 9:
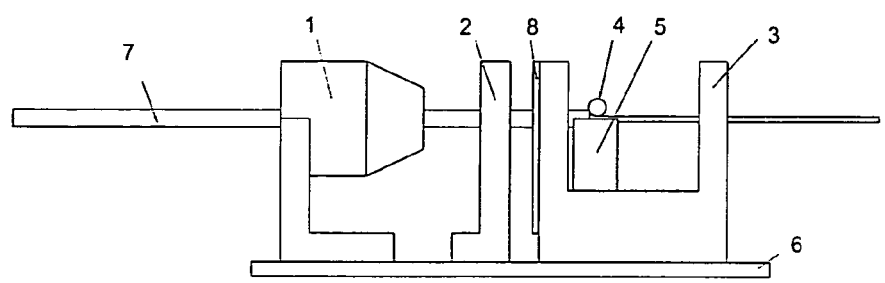
FIG. 9 shows a plan view of the HSC milling machine shown in FIG. 8.

In FIGS. 6 and 7, the milling cutter 4 is set centrally but at an angle.

The milling cutter positions shown in FIGS. 1 to 7 are primarily suitable for forming flutes. A cylindrical milling cutter 4 is used in FIGS. 8 and 9. This arrangement allows material to be removed in particular from the circumference. This is also possible in the arrangements shown in FIGS. 1 to 5, by using an end milling cutter.

Figure 10:
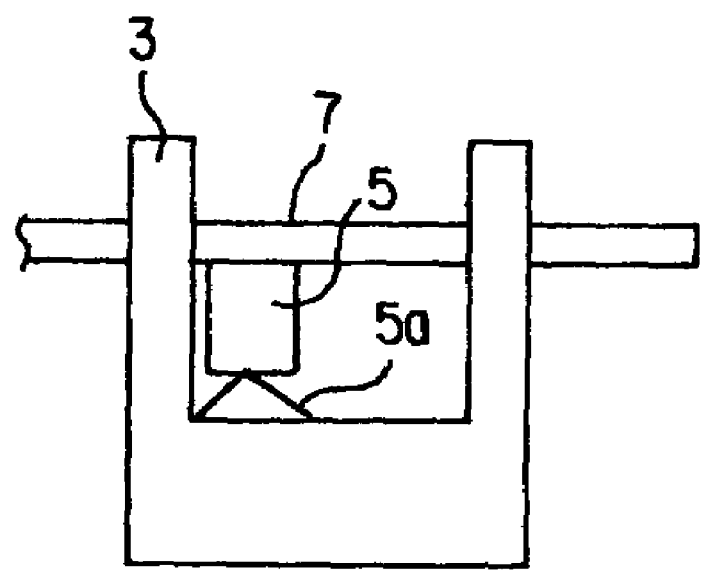
FIG. 10 shows a support device with a spring to support the blank.

In the exemplary embodiment shown in FIG. 10, the support device 5 is provided with a spring 5a to elastically and radially support the blank.

The following parameters have proven practical for the machining: depending on the size of the milling cutter, the cutting speed $V_C$ can be selected between 20 and 200 m/min, the feed $f_Z$ per tooth or cutting edge of the milling cutter is expediently between 0.5 and 100 μm/tooth (combined movement comprising linear feed and rotation of the blank), the preferred values being $V_C$ roughly≈50 m/min and $f_Z$ roughly≈5 μm.

What is claimed is:

1. A method of making an endodontic instrument from a rod form blank of a nickel-titanium alloy, comprising:
    milling said rod form blank using a high speed cutting process and a geometrically defined cutting edge of a milling cutter to shape said instrument by cutting material therefrom.

2. A method according to claim 1, wherein said milling is performed at a cutting speed in the range of 10 m/min to 300 m/min.

3. A method according to claim 1, wherein said milling is performed with the milling cutter fitted eccentrically above a longitudinal axis of the blank.

4. A method according to claim 2, wherein said milling is performed with the milling cutter fitted eccentrically above a longitudinal axis of the blank.

5. A method according to claim 1, comprising supporting the blank with a lateral guide at a side opposite the milling cutter during said milling.

6. A method according to claim 2, comprising supporting the blank with a lateral guide at a side opposite the milling cutter during said milling.

7. A method according to claim 3, comprising supporting the blank with a lateral guide at a side opposite the milling cutter during said milling.

8. A method according to claim 4, comprising supporting the blank with a lateral guide at a side opposite the milling cutter during said milling.

9. A method according to claim 1, wherein the lateral guide elastically supports the blank during said milling.

10. A method for machining and/or manufacturing endodontic instruments from a blank in rod or wire form, in which a milling method using a geometrically defined cutting edge and cutting removal is used for shaping.

11. The method as claimed in claim 10, in which a high-speed-cutting milling method is used.

12. The method as claimed in claim 10, in which the cutting speed $V_C$ is in the range from 10 m/min to 300 m/min.

13. The method as claimed in claim 10, in which the blank is configured from a nickel-titanium alloy.

14. The method as claimed in claim 10, in which a milling cutter is fitted eccentrically above the workpiece longitudinal axis.

15. The method as claimed in claim 10, in which the blank is supported on the side which lies opposite a milling cutter.

16. The method as claimed in claim 15, in which the blank is supported elastically.

17. The method as claimed in claim 15, in which the support for the blank comprises a lateral guide.

18. A method according to claim 4, wherein the lateral guide elastically supports the blank during said milling.

19. An endodontic instrument made by the method of claim 1.

* * * * *